(12) United States Patent
Regensburger

(10) Patent No.: US 11,941,765 B2
(45) Date of Patent: Mar. 26, 2024

(54) REPRESENTATION APPARATUS FOR DISPLAYING A GRAPHICAL REPRESENTATION OF AN AUGMENTED REALITY

(71) Applicant: Siemens Healthcare GmbH, Erlangen (DE)

(72) Inventor: Alois Regensburger, Poxdorf (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 17/834,918

(22) Filed: Jun. 7, 2022

(65) Prior Publication Data

US 2022/0414994 A1 Dec. 29, 2022

(30) Foreign Application Priority Data

Jun. 24, 2021 (DE) .................. 10 2021 206 565.1

(51) Int. Cl.
*G06T 19/00* (2011.01)
*G02B 27/01* (2006.01)
*G06T 15/20* (2011.01)

(52) U.S. Cl.
CPC ........ *G06T 19/006* (2013.01); *G02B 27/0101* (2013.01); *G06T 15/20* (2013.01); *G02B 2027/0138* (2013.01); *G02B 2027/014* (2013.01); *G06T 2200/08* (2013.01); *G06T 2210/41* (2013.01)

(58) Field of Classification Search
CPC ... G06T 19/006; G06T 15/20; G06T 2200/08; G06T 2210/41; G02B 27/0101

USPC .......................................................... 345/419
See application file for complete search history.

(56) References Cited

U.S. PATENT DOCUMENTS

| | | | |
|---|---|---|---|
| 8,681,256 B2 * | 3/2014 | Sako ..................... | G06T 11/001 348/333.02 |
| 9,626,799 B2 * | 4/2017 | McArdle ............. | G06F 3/04883 |
| 2013/0290876 A1 * | 10/2013 | Anderson ............. | G06T 19/006 715/761 |

(Continued)

FOREIGN PATENT DOCUMENTS

| | | |
|---|---|---|
| DE | 102021205700 A1 | 12/2022 |
| JP | 2020508828 A | 3/2020 |
| WO | 2021061441 A1 | 4/2021 |

*Primary Examiner* — Thomas J Lett
(74) *Attorney, Agent, or Firm* — Lempia Summerfield Katz LLC

(57) ABSTRACT

A representation apparatus for displaying a graphical representation of an augmented reality includes a capture unit, a first display unit, and a processing unit. The first display unit is at least partially transparent. The capture unit is configured to capture a relative positioning of the first display unit relative to a representation area of a second display unit. The processing unit is configured to determine an observation geometry between the first display unit and the representation area of the second display unit based on the relative positioning, receive a dataset, generate the augmented reality based on the dataset, and provide the graphical representation of the augmented reality via virtual mapping of the augmented reality onto the representation area along the observation geometry. The first display unit displays the graphical representation of the augmented reality in at least partial overlaying with the representation area of the second display unit.

18 Claims, 6 Drawing Sheets

(56) References Cited

U.S. PATENT DOCUMENTS

| | | | |
|---|---|---|---|
| 2018/0164983 A1* | 6/2018 | Torii | G06F 3/011 |
| 2018/0293041 A1 | 10/2018 | Harviainen | |
| 2019/0164334 A1* | 5/2019 | Denman | G06T 15/205 |
| 2019/0365498 A1 | 12/2019 | Gibby et al. | |
| 2020/0036910 A1 | 1/2020 | Alzaga et al. | |
| 2020/0107888 A1 | 4/2020 | Suchy | |
| 2021/0096638 A1 | 4/2021 | O'hern et al. | |
| 2021/0150803 A1* | 5/2021 | Denman | G06T 19/006 |
| 2022/0138997 A1* | 5/2022 | Kim | G06F 3/16 |
| | | | 345/633 |

\* cited by examiner

REPRESENTATION APPARATUS FOR DISPLAYING A GRAPHICAL REPRESENTATION OF AN AUGMENTED REALITY

This application claims the benefit of German Patent Application No. DE 10 2021 206 565.1, filed on Jun. 24, 2021, which is hereby incorporated by reference in its entirety.

BACKGROUND

The present embodiments relate to a representation apparatus for displaying a graphical representation of an augmented reality, a system, and a method for providing a graphical representation of an augmented reality.

For the realistic representation of medical information (e.g., medical image data from an examination object), representations of an augmented reality (AR) are increasingly being used. Herein, real objects (e.g., medical objects and/or an examination object) are often displayed overlaid with virtual data (e.g., medical image data and/or virtual objects) and represented in a display. For a realistic representation with a high degree of immersion, a precise registration between the virtual data and the real objects is to be provided.

A graphical representation of preoperative and/or intraoperative image data of an examination object in augmented reality may be used to assist a medical personnel member (e.g., a medical practitioner) during interventional and/or surgical procedures. However, it is often disadvantageous therein that the image data to be displayed by the apparatus for representing the augmented reality is to be received and processed by a providing unit and/or a medical imaging device (e.g., in real time). This may be limited in a disadvantageous manner in the case, for example, of a simultaneous provision of the image data to a plurality of apparatuses for representing an augmented reality, by an available transfer bandwidth. Further, an image quality of the image data to be displayed by the apparatus for representing the augmented reality may thereby be disadvantageously reduced. A delay between the recording of the, for example, intraoperative image data of the examination object and its display in the augmented reality and/or the reduced image quality may lead to a faulty coordination during the interventional and/or surgical procedure. As a result, a risk of injury to the examination object may be increased.

In a medical environment, it is often necessary that three-dimensionally (3D) resolved image data of the examination object may be observed simultaneously by a plurality of observers among the medical personnel. For this purpose, for example, a 3D monitor in combination with stereoscopic filter goggles that may be worn by the medical personnel may be used. The 3D monitor may therein provide two individual stereoscopic images that may be captured for a plurality of observers among the medical personnel by the filter goggles. A disadvantage, however, is the lack of adaptation of the stereoscopic single images to the, for example, momentary observation points of the plurality of observers. As a result and, for example, dependent upon the observation points, an unrealistic and/or insufficient depth perception may arise during the observation of the three-dimensionally resolved image data on the 3D monitor.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved adaptation of an augmented reality is provided.

In a first aspect, a representation apparatus for displaying a graphical representation of an augmented reality is provided. Therein, the representation apparatus has a capture unit, a first display unit, and a processing unit. Further, the first display unit is configured to be at least partially transparent. The capture unit is configured to capture a relative positioning of the first display unit relative to a representation area of a second display unit. The representation area of the second display unit is therein configured to display graphical information. The processing unit is configured to determine an observation geometry between the first display unit and the representation area of the second display unit based on the relative positioning. In addition, the processing unit is configured to receive a dataset. Further, the processing unit is configured to generate the augmented reality based on the dataset. The processing unit is also configured to provide the graphical representation of the augmented reality via a virtual mapping of the augmented reality onto the representation area of the second display unit along the observation geometry. In addition, the first display unit is configured to display the graphical representation of the augmented reality in at least partial overlay with the representation area of the second display unit.

The second display unit may include, for example, a screen and/or a monitor and/or a projector and/or a projection area. Therein, the representation area of the second display unit may include the projection area and/or a display layer (e.g., panel) of the screen and/or the monitor. For example, the representation area of the second display unit may include a spatially limited area (e.g., coherent area) on which the graphical information may be displayed. Therein, the representation area of the second display unit may extend, at least partially (e.g., completely) flat (e.g., planar or curved). The graphical information may include image data (e.g., medical image data) and/or text information (e.g., operating parameters and/or object parameters of an object (medical object)) and/or metadata regarding the medical image data.

The capture unit may be configured to capture a spatial positioning of the first display unit and the second display unit (e.g., the representation area of the second display unit). The spatial positioning of the first display unit and the second display unit may each include a spatial position and/or alignment of the first display unit and the second display unit in a coordinate system of the capture unit. The capture unit may be further configured to capture the relative positioning of the first display unit in relation to the representation area of the second display unit based on the captured spatial positioning of the first display unit and the second display unit. The relative positioning of the first display unit in relation to the representation area of the second display unit may include an item of information regarding a spatial distance between the first display unit (e.g., an origin of the coordinate system of the first display unit) and the representation area of the second display unit (e.g., a reference point, such as a midpoint or corner point of the representation area). Further, the relative positioning may include an item of information regarding an angle (e.g., a viewing angle) of the first display unit in relation to the representation area of the second display unit (e.g., in relation to a normal vector in the reference point of the representation area).

Alternatively, the capture unit may be configured to capture the relative positioning of the first display unit or the second display unit (e.g., the representation area of the second display unit) in relation to the other display unit. Therein, the capture unit may be arranged in a defined manner in relation to first display unit or the second display unit (e.g., fastened to the first display unit or the second display unit) and/or may be at least partially (e.g., completely) integrated into the first display unit or the second display unit. By this, the capture unit may be configured to directly capture the relative positioning of the representation area of the second display unit in relation to the first display unit. Therein, the relative positioning of the first display unit in relation to the representation area of the second display unit may describe a, for example, three-dimensional spatial position and orientation of the representation area in a coordinate system of the first display unit.

The processing unit may be further configured to determine the observation geometry between the first display unit (e.g., one or more observation points, such as eyes, of a user looking through the first display unit in one operating state of the representation apparatus) and the representation area of the second display unit based on the relative positioning. Therein, the observation geometry may describe an optical ray path between the representation area of the second display unit and the first display unit (e.g., the one or more observation points of the user). For example, the observation geometry may describe, in the operating state of the representation apparatus, the optical ray path from the graphical information displayed on the representation area of the second display unit, through the first display unit (e.g., the graphical representation of the augmented reality), to the one or more observation points (e.g., the eyes of the user looking through the first display unit). By this, the observation geometry may describe the optical ray path of an overlaid observation of the graphical information that may be displayed on the second display unit with the graphical representation of the augmented reality starting from the one or more observation points of the user.

The processing unit may be coupled communicatively to the first display unit and the capture unit (e.g., wirelessly or cable-bound). The reception of the dataset may include, for example, a capture and/or readout of a computer-readable data store and/or a reception from a data storage unit (e.g., a database). Further, the dataset may be provided by a medical imaging device. For this purpose, the processing unit may have an interface.

The dataset may include image data (e.g., medical image data) and/or image parameters (e.g., metadata) and/or model data (e.g., a patient and/or organ and/or tissue model) and/or model parameters and/or text data (e.g., operating parameters) and/or object parameters (e.g., medical object parameters) and/or patient information (e.g., history data and/or diagnosis data and/or physiological information and/or procedural data, such as an item of information for a surgery phase).

The processing unit may be configured to generate the augmented reality having at least one virtual object (e.g., a plurality of virtual objects based on the dataset). Therein, the augmented reality may include, for example, a two-dimensional and/or three-dimensional virtual arrangement of the at least one virtual object (e.g., the plurality of virtual objects in the coordinate system of the first display unit). In one embodiment, the processing unit may be configured to generate the at least one virtual object having geometrical and/or anatomic and/or textual and/or graphical features of the dataset. Further, the processing unit may be configured to register the augmented reality (e.g., the at least one virtual object) to the representation area of the second display unit.

The processing unit may also be configured to provide the graphical representation of the augmented reality (e.g., a graphical representation of the at least one virtual object via a virtual mapping of the augmented reality, such as the at least one virtual object) onto the representation area of the second display unit along the observation geometry. Therein, the graphical representation may include, for example, a two-dimensional and/or three-dimensional representation (e.g., stereoscopic representation) of the augmented reality on the first display unit. Therein, the graphical representation of the augmented reality may be arranged, for the user who looks through the first display unit, virtually on the representation area of the second display unit. The virtual mapping of the augmented reality onto the representation area of the second display unit along the observation geometry may include, for example, a virtual arrangement of the at least one virtual object on the representation area of the second display unit along the observation geometry. In addition, the virtual mapping for providing the graphical representation of the augmented reality may be based, for example, on a virtual projection mapping and/or ray-tracing and/or a rendering according to a mapping matrix (e.g., a camera matrix) of the at least one virtual object onto the representation area of the second display unit along the observation geometry. Further, the virtual mapping of the augmented reality onto the representation area of the second display unit may include a virtual illumination and/or a virtual shadow of the at least one virtual object according to the observation geometry (e.g., momentary observation geometry). Further, the processing unit may be configured to adapt a stereo disparity of the virtual mapping dependent on the observation geometry for a stereoscopic display of the graphical representation of the augmented reality by the first display unit. In addition, the graphical representation of the augmented reality may have context information (e.g., an item of patient information and/or a workflow indication) that is virtually arranged outside the representation area of the second display unit (e.g., adjoining the representation area and/or in a plane with the representation area).

The provision of the graphical representation of the augmented reality may include a storage on a computer-readable storage medium (e.g., a non-transitory computer-readable storage medium) and/or a transfer to a first display unit.

The first display unit may be configured to display the graphical representation of the augmented reality (e.g., two-dimensionally or three-dimensionally). For example, the first display unit may be configured for stereoscopic display of the graphical representation of the augmented reality. The first display unit may be configured to represent real (e.g., physical) objects (e.g., the representation area of the second display unit), with the graphical representation of the augmented reality (e.g., a graphical representation of the at least one virtual object) at least partially overlaid and in a display. For this purpose, the first display unit may include, for example, a screen and/or a monitor and/or a projector and/or a projection area. In one embodiment, the first display unit may be configured as goggles (e.g., data goggles) and/or a helmet (e.g., a data helmet). Further, the first display unit may be configured to be portable (e.g., wearable by a user). Therein, the first display unit may follow a movement of the user (e.g., a head movement of the user). Further, the first display unit may be configured at least partially light-transmitting (e.g., translucent and/or transparent). Further, the first display unit may be configured to be arranged in a field of view of the user.

The embodiment may enable a display of the graphical representation of the augmented reality adapted to the observation geometry (e.g., momentary observation geometry) of the user. Therein, the graphical representation of the augmented reality may at least partially overlay the graphical information that the second display unit displays on its representation area in an operating state of the representation apparatus. Further, in the operating state of the representation apparatus, the second display unit may display the graphical information from the display of the graphical representation of the augmented reality uninfluenced (e.g., free from distortion and/or in a higher image quality) on the representation area of the second display unit.

In a further embodiment of the representation apparatus, the processing unit may be configured, in the case of a changed relative positioning, to determine repeatedly the observation geometry between the first display unit and the representation area of the second display unit. Further, the processing unit may be configured, with the changed relative positioning, to provide the graphical representation of the augmented reality based on the most recently determined observation geometry.

The capture unit may be configured to capture directly the relative positioning of the first display unit in relation to the representation area of the second display repeatedly (e.g., continuously). Further, the processing unit may be configured to identify a deviation between a most recently captured and a previously captured relative positioning of the first display unit in relation to the representation area of the second display unit. Therein, the identification of the deviation may include a comparison between the most recently and the previously captured relative positioning. Further, the processing unit may be configured to determine repeatedly the observation geometry (e.g., based on the most recently captured relative positioning). Further, the processing unit may be configured to provide the graphical representation of the augmented reality based on the most recently determined observation geometry. For example, the processing unit may be configured to provide the graphical representation of the augmented reality via the virtual mapping of the augmented reality onto the representation area of the second display unit along the most recently determined observation geometry.

By this, the graphical representation of the augmented reality may be adapted to the relative positioning that has been changed (e.g., by a movement of the user).

In a further embodiment of the representation apparatus, the capture unit may be arranged, spaced from the first display unit and the second display unit or at least partially (e.g., completely) integrated into the first display unit or the second display unit.

In a first variant, the capture unit may be arranged, spaced from the first display unit and the second display unit (e.g., positionally fixed in relation to a room in which the first display unit and the second display unit are arranged in an operating state of the representation apparatus). In one embodiment, the capture unit may be arranged (e.g., positioned), such that the first display unit and the second display unit are arranged, in the operating state of the representation apparatus, in a capture region of the capture unit. By this, the capture unit may be configured to capture the spatial positioning of each of the first display unit and the second display unit (e.g., simultaneously).

In a second variant, the capture unit may be integrated at least partially into the first display unit or at least partially into the second display unit. Therein, the capture unit may have a defined (e.g., positionally fixed) arrangement in relation to the first display unit or the second display unit (e.g., the representation area of the second display unit). In one embodiment, the capture unit may be integrated at least partially into the first display unit or the second display unit such that the respective other display unit is arranged, in the operating state of the representation apparatus, in the capture region of the capture unit. By this, the capture unit may be configured to capture directly the relative positioning between the first display unit and the second display unit.

In an arrangement of the capture unit spaced from the first display unit (e.g., in an at least partial integration of the capture unit into the second display unit), the capture unit may be configured for capture (e.g., simultaneous capture) of the respective spatial positioning (e.g., the relative positioning of each representation apparatus of a plurality of similar or different representation apparatuses).

In a further embodiment of the representation apparatus, the capture unit may include an optical and/or electromagnetic and/or acoustic sensor for capturing the relative positioning.

For example, the capture unit may have an optical sensor configured as a camera (e.g., a 2D camera and/or an omnidirectional camera and/or a 3D camera, such as a stereo camera and/or a depth camera and/or a time-of-flight (TOF) camera) that is designed for at least partial (e.g., optical) capture of the first display unit and/or the second display unit. Further, the capture unit may have an electromagnetic sensor that may be configured to locate the first display unit and/or the second display unit based on electromagnetic waves (e.g., a change and/or interference of electromagnetic waves). The electromagnetic sensor may further be configured as a gyroscopic sensor for capturing a spatial positioning of the capture unit (e.g., if the capture unit is integrated at least partially into the first display unit or the second display unit). Further, the capture unit may have an acoustic (e.g., ultrasound-based) sensor that is configured to emit a defined ultrasonic field and to capture the relative positioning based on a reflected portion of the ultrasonic field. In one embodiment, the capture unit may be configured to provide a signal dependent upon the captured relative positioning of the first display unit in relation to the representation area of the second display unit to the processing unit.

The embodiment may enable a precise capture of the relative positioning of the first display unit in relation to the representation area of the second display unit.

In a further embodiment of the representation apparatus, the capture unit may be configured to capture the relative positioning based on physical features of the first display unit and/or the second display unit and/or based on a graphical marker structure displayed visibly and/or invisibly on the representation area of the second display unit.

The physical features of the first display unit and/or the second display unit may include, for example, a contour and/or a shape and/or a material property and/or a texture (e.g., a reflectivity and/or absorptivity). Further, the first display unit and/or the second display unit may have a physical (e.g., two-dimensional or three-dimensional) marker structure that is fastened in a defined arrangement on the first display unit and/or second display unit and/or is integrated at least partially into the first display unit and/or second display unit (e.g., on an edge and/or frame of the first display unit and/or the second display unit). In one embodiment, the capture unit may be configured for capturing a spatial positioning (e.g., a spatial position and/or orientation and/or posture) of the respective marker structure.

Alternatively or additionally, the second display unit may be configured to display a graphical marker structure (e.g., for a human user) visibly and/or non-visibly. The graphical marker structure may include an arrangement of graphical position markers of, for example, a geometrical form and/or a defined pattern that is stationary (e.g., in relation to the representation area of the second display unit). The capture unit may be configured to capture the graphical marker structure that is displayed in the operating state of the representation apparatus on the representation area of the second display unit. The capture unit may further be configured to capture the relative positioning of the first display unit in relation to the representation area of the second display unit based on the captured graphical marker structure (e.g., based on a spatial positioning of the graphical marker structure).

The second display unit may be configured to display the graphical marker structure visibly (e.g., at least partially with the graphical information overlaid and/or at least partially integrated into the graphical information).

Alternatively or additionally, the second display unit may be configured to display the graphical marker structure non-visibly. Therein, the display of the graphical marker structure may take place in a wavelength region outside a light spectrum perceptible to the human user (e.g., in an infrared region). Alternatively or additionally, the second display unit may be configured to display a graphical marker structure temporally and/or spatially interlaced with the graphical information. The temporal interlacing may describe a display (e.g., repeated display) of the graphical marker structure within a temporal sequence of the display of the graphical information. Therein, the second display unit may be configured to display the graphical marker structure so seldom and/or briefly within the sequence of the display of the graphical information that the graphical marker structure is not perceptible to the human user. The spatially interlaced display of the graphical marker structure with the graphical information may take place, for example, line by line and/or column by column. Therein, the second display unit may be configured to specify a spatial resolution of the graphical marker structure such that the graphical marker structure in the spatially interlaced display is not perceptible to the human user. In one embodiment, the second display unit may be configured to display the graphical marker structure without any influence that is perceptible to the human user on the graphical information.

The embodiment may enable a particularly robust and simultaneously precise capture of the relative positioning of the first display unit in relation to the representation area of the second display unit.

In a further embodiment of the representation apparatus, the graphical representation of the augmented reality may have a graphical representation of at least one virtual object of the augmented reality. Further, the capture unit may be configured to determine an observation parameter based on the relative positioning. Further, the processing unit may be configured to determine the at least one virtual object based on the observation parameter. Alternatively or additionally, the processing unit may be configured to adapt a resolution and/or scaling and/or size and/or positioning of the graphical representation of the at least one virtual object based on the observation parameter.

The observation parameter determined based on the relative positioning may describe one or more properties of the observation geometry (e.g., not user-specifically). For example, the observation parameter may include an item of information regarding, for example, a momentary spatial distance between the first display unit (e.g., the origin of the coordinate system of the first display unit) and the representation area of the second display unit (e.g., the reference point, such as the midpoint or the corner point of the representation area). Further, the observation parameter may include an item of information regarding the angle (e.g., the viewing angle) of the first display unit in relation to the representation area of the second display unit (e.g., the normal vector in the reference point of the representation area). Further, the observation parameter may include an item of information regarding the spatial extent (e.g., a fan angle) of the field of view of the first display unit in relation to the representation area of the second display unit.

The processing unit may be configured to determine the at least one virtual object based on the observation parameter. Therein, the determination of the at least one virtual object may include, for example, a filtration of, for example, content and/or graphics and/or a reconstruction of the dataset. The filtration of the dataset may include, for example, a selection of elements and/or features and/or information of the dataset based on the observation parameter for determining the at least one virtual object of the dataset. Alternatively or additionally, the processing unit may be configured to adapt the, for example, spatial and/or temporal resolution and/or scaling and/or the size and/or the positioning of the graphical representation of the at least one virtual object based on the observation parameter. For example, the processing unit may be configured to reduce the spatial resolution of the graphical representation of the at least one virtual object with increasing spatial distance between the first display unit and the representation area of the second display unit. In addition, the processing unit may be configured to reduce the graphical representation of the at least one virtual object with increasing spatial distance between the first display unit and the representation area of the second display unit, for example, by scaling. In addition, the processing unit may be configured to adapt the positioning (e.g., the position and/or orientation) of the graphical representation of the at least one virtual object on the representation area of the second display unit dependent upon the observation parameter (e.g., the viewing angle). The processing unit may further be configured for adapting further representation parameters of the graphical representation of the at least one virtual object based on the observation parameter (e.g., a script size and/or a line thickness and/or a color coding and/or a grey scale coding).

The embodiment may enable an immersive and realistic display of the graphical representation of the augmented reality (e.g., of the at least one virtual object in the at least partial overlaying with the representation area of the second display unit).

In a further embodiment of the representation apparatus, the capture unit may be configured to capture an input and/or identification of a user who looks through the first display unit in an operating state of the representation apparatus. Further, the capture unit may be configured to determine the observation parameter additionally based on the input and/or identification of the user (e.g., user-specifically).

The sensor of the capture unit for capturing the relative positioning may also be configured to capture the input of the user. Alternatively or additionally, the capture unit may have a further sensor (e.g., optical and/or electromagnetic and/or acoustic and/or haptic) that is configured to capture the input of the user. The capture unit may also be configured to capture the input of the user by use of an input device. The input device may include, for example, a pointing device (e.g., a stylus and/or a marker structure) and/or an input unit (e.g., a keyboard) and/or a body part of the user (e.g., a hand and/or a finger) and/or an optical and/or acoustic signal. In one embodiment, the capture unit may be configured for two-dimensional and/or three-dimensional spatial capture of the input of the user, for example, based on the input device. For example, the capture unit may be configured to capture the input of the user point-wise and/or in a time resolved manner (e.g., as a trajectory and/or a gesture).

The input by the user may have an item of information (e.g., at least one input parameter for the determination of the at least one virtual object and/or the adaptation of the resolution and/or scaling and/or the size and/or positioning of the graphical representation of the at least one virtual object). For example, the input by the user may have a criterion for the selection of elements and/or features and/or information of the dataset for determining the at least one virtual object.

Further, the capture unit may be configured to capture the identification of the user. The capture unit may be configured to capture the identification of the user using the sensor of the capture unit for capturing the relative positioning and/or using the further sensor. The capture of the identification of the user may take place, for example, using biometric features (e.g., a voice profile and/or a fingerprint and/or using the input of the user and/or using an identification medium, such as a barcode and/or a radio frequency identification (RFID) system). The processing unit may be configured to assign a role based on the identification of the user. The different roles of the user may be classified, for example, based on an observation interest (e.g., medical observation interest) and/or an interaction level and/or an expertise of the respective user.

The processing unit may be configured to generate the augmented reality at least partially differently for different identifications (e.g., roles) of users. Further, the processing unit may be configured to provide the graphical representation of the augmented reality at least partially differently for different identifications (e.g., roles) of users. The capture unit may be configured to determine (e.g., to select) the observation parameter additionally based on the identification (e.g., the role) of the user. In one embodiment, the capture unit may determine at least one observation parameter regarding the classified roles of users via a capture and/or a readout of a computer-readable data store and/or a reception from a data storage unit (e.g., a database). The observation parameter may have, for example, the user-specific and/or role-specific criterion for the selection of elements and/or features and/or information of the dataset for determining the at least one virtual object. Alternatively or additionally, the observation parameter may have a, for example, user-specific and/or role-specific instruction regarding the resolution and/or scaling and/or size and/or positioning of the graphical representation of the at least one virtual object. Further, the, for example, user-specific observation parameter may have an item of information regarding a user specific stereo disparity. Therein, the processing unit may be configured to adapt the virtual mapping for providing the graphical representation of the augmented reality (e.g., for a stereoscopic display of the graphical representation of the augmented reality based on the observation parameter to the user-specific stereo disparity).

The embodiment may enable a user-specific and/or context-sensitive adaptation (e.g., manual adaptation) of the graphical representation of the augmented reality (e.g., of the at least one virtual object).

In a further embodiment of the representation apparatus, the dataset may have a parameter relating to the graphical information that the second display unit displays in an operating state of the representation apparatus on the representation area. Therein, the processing unit may further be configured to generate the augmented reality dependent upon the parameter.

The parameter may have an item of origin information and/or an item of representation information regarding the graphical information that displays the second display unit in the operating state of the representation apparatus. Therein, the origin information may have, for example, an item of information relating to a source of the graphical information (e.g., a medical imaging device for recording and/or for providing the graphical information). For example, the parameter may have metadata relating to the graphical information. Further, the origin information may have a recording parameter and/or a reconstruction parameter relating to the graphical information. In addition, the origin information may have an item of positioning information relating, for example, to a spatial position and/or orientation and/or posture and/or a spatial recording region of the source (e.g., of the medical imaging device) for recording and/or for providing the graphical information. The representation information may further have an item of information regarding the display of the graphical information (e.g., an image frequency and/or a resolution and/or an encoding of image values, such as a color-coding or a gray-scale coding).

The processing unit may further be configured to generate the augmented reality dependent upon the parameter. For example, the processing unit may be configured to determine the at least one virtual object (e.g., the plurality of virtual objects) dependent upon the parameter. Further, the processing unit may be configured to adapt the virtual arrangement of the at least one virtual object (e.g., the plurality of virtual objects) in the coordinate system of the first display unit dependent upon the parameter. By this, the positioning of the graphical representation of the at least one virtual object may be adapted to the representation area of the second display unit dependent upon the parameter. For example, the processing unit may be configured to register the augmented reality (e.g., the at least one virtual object) based on the observation geometry and the parameter with the graphical information. The processing unit may further be configured to adapt the graphical representation of the augmented reality (e.g., the at least one virtual object dependent upon the parameter).

By this, an improved immersion of the graphical representation of the augmented reality in the at least partial overlaying with the graphical information displayed on the representation area of the second display unit in the operating state may be enabled.

In a further embodiment of the representation apparatus, the dataset may have first medical image data. Therein, the processing unit may be configured to generate the augmented reality based on the first medical image data. In one embodiment, in the operating state of the representation apparatus, the second display unit may display a graphical representation of second medical image data on the representation area as the graphical information. Therein, the first medical image data and the second medical image data may have a mapping and/or a model of an at least partial shared examination region (e.g., common examination region) of an examination object. Further, in the operating state of the representation apparatus, the graphical representation of the augmented reality may be at least partially overlaid with the graphical representation of the second medical image data.

The first medical image data and/or the second medical image data may be recorded and/or provided by a medical imaging device or different medical imaging devices. The at least one medical imaging device may be configured for recording the first medical image data and/or the second medical image data, for example, as a medical X-ray device and/or a magnetic resonance (MRT) system and/or a computed tomography (CT) system and/or a positron emission tomography (PET) system and/or an ultrasonography device and/or an endoscope (e.g., a laparoscope and/or a bronchoscope and/or catheter). Therein, the first medical image data and the second medical image data may be the same or different with regard to recording parameters and/or reconstruction. Further, the first medical image data and the second medical image data may be registered to one another.

In one embodiment, the first medical image data may have a two dimensional or three-dimensional spatially resolved (e.g., and time resolved) mapping of at least a first examination region (e.g., an anatomical region and/or an organ, such as a hollow organ and/or a bone structure of the examination object). Further, the second medical image data may have a two dimensional or three-dimensional spatially resolved (e.g., and time resolved) mapping of at least a second examination region (e.g., an anatomical region and/or an organ, such as a hollow organ and/or a bone structure of the examination object). The first medical image and/or the second medical image data may have, for example, a scene (e.g., a surgical video). Therein, the first examination region and the second examination region may match at least partially. By this, the first medical image data and the second medical image data may at least partially map a shared examination region of the examination object. The first medical image data and/or second medical image data may each have a contrasted and/or segmented mapping of the examination object (e.g., the first examination region and/or the second examination region). The examination object may be, for example, a human and/or animal patient and/or an examination phantom. Further, the first medical image data and the second medical image data may map the examination object (e.g., the shared examination region) at different or at least partially the same recording time points (e.g., preoperatively and/or intraoperatively). Further, the first medical image data may have a, for example, intraoperative mapping of the medical imaging device (e.g., in an embodiment as an endoscope and/or a catheter) for recording the second medical image data, or vice versa.

Alternatively or additionally, the first medical image data and/or the second medical image data may have a 2D and/or 3D model (e.g., a centerline model and/or a volume model, such as a volume mesh model) of the respective examination region (e.g., of the hollow organ).

The processing unit may be configured to generate the augmented reality based on the first medical image data. For example, the processing unit may be configured to determine the at least one virtual object by segmentation and/or identification of anatomical objects (e.g., a tissue region and/or an organ, such as a hollow organ and/or medical objects, such as a surgical and/or diagnostic instrument and/or an implant) that are mapped in the first medical image data. The at least one virtual object may have, for example, a mapping and/or a virtual representation (e.g., a 2D or 3D model) of the segmented and/or identified anatomical and/or medical objects.

The second display unit may be configured to display the graphical representation of the second medical image data as the graphical information in the operating state of the representation apparatus. Further, the processing unit may be configured to provide the graphical representation of the augmented reality such that the graphical representation of the augmented reality displayed by the first display unit in the operating state of the representation apparatus is at least partially overlaid with the graphical representation of the second medical image data on the representation area of the second display unit. For example, the processing unit may be configured to provide the graphical representation of the augmented reality such that the at least partially shared region of the examination object is arranged congruently in the overlay of the graphical representation of the second medical image data with the graphical representation of the augmented reality. For example, the processing unit may be configured to register the graphical representation of the augmented reality with the graphical representation of the second medical image data based on the relative positioning (e.g., the observation geometry).

The embodiment may enable an at least partially overlaid display of the graphical representation of the augmented reality with the graphical representation of the second medical image data displayed on the representation area of the second display unit in the operating state. Therein, the display of the graphical representation of the second medical image data (e.g., with regard to image quality and/or a display delay) may remain uninfluenced by the display of the graphical representation of the augmented reality.

In a further embodiment of the representation apparatus, the first image data may map and/or model the examination object three-dimensionally. Further, the processing unit may be configured to provide the graphical representation of the augmented reality having a virtual window relating to the graphical representation of the second image data.

In one embodiment, the processing unit may be configured to determine and/or identify a region of interest (e.g., two-dimensional region of interest) on the representation area of the second display unit (e.g., in the second medical image data). Therein, the processing unit may be configured to determine and/or identify the region of interest, for example, based on a further input by the user and/or based on geometrical features (e.g., a contour and/or an image value and/or a contrast value and/or anatomical features, such as a tissue boundary and/or a vessel wall and/or a marker structure of the second medical image data). In one embodiment, the region of interest may delimit at least one part (e.g., coherent and/or spatially limited) of the representation area of the second display unit on which the virtual window is to be positioned in the graphical representation of the augmented reality.

The virtual window may describe a spatially limited and/or coherent region of the graphical representation of the augmented reality that, in the at least partial overlaying with the representation area of the second display unit, has a virtual transparency in relation to the graphical representation of the second medical image data. In one embodiment, the processing unit may be configured to arrange the graphical representation of the augmented reality (e.g., the graphical representation of the at least one virtual object) on the region of interest on the representation area of the second display unit. The processing unit may be configured to provide the virtual window two-dimensionally or three-dimensionally spatially resolved. The virtual window may further have a, for example, two-dimensionally or three-dimensionally spatially resolved region of the first medical image data. In one embodiment, the processing unit may be configured to provide the graphical representation of the augmented reality such that the at least partially shared region of the examination object (e.g., shared geometrical and/or anatomical features) in the overlaying of the graphical representation of the second medical image data with the graphical representation of the augmented reality (e.g., the virtual window) is arranged congruently. The processing unit may also be configured to adapt the virtual window (e.g., the region of the first medical image data dependent upon the momentary observation geometry). Further, the processing unit may be configured to adapt the virtual window dependent upon the observation parameter and/or the parameter relating to the graphical information (e.g., the second medical image data). The adaptation of the virtual window dependent upon the observation geometry may include the virtual mapping of the augmented reality onto the representation area of the second display unit (e.g., the region of interest) having a depth dimension in relation to the representation area. Therein, the virtual mapping of the augmented reality (e.g., the at least one virtual object) onto the representation area (e.g., on a virtual projection mapping and/or ray-tracing and/or a rendering in accordance with a mapping matrix, such as a mapping matrix and/or camera matrix of the medical imaging device for recording and/or for providing the first medical image data) may be based along the observation geometry. Further, the depth dimension may extend substantially perpendicularly to the representation area of the second display unit. For example, the region of interest on the representation area of the second display unit may delimit the spatial region of the transparency that is provided by the overlaying with the graphical representation of the augmented reality (e.g., the virtual window).

The embodiment may enable an immersive observation of the first medical image data in the graphical representation of the augmented reality via the virtual window in the representation area of the second display unit.

In a further embodiment of the representation apparatus, the shared region of the examination object may have a bordered hollow space. Therein, the virtual window may be delimited by the bordering of the hollow space cut from a virtual plane in the virtual mapping of the augmented reality onto the representation area of the second display unit.

The bordered hollow space may denote a spatially delimited space (e.g., a fluid-filled hollow space) of the examination object, spatially delimited, for example, by a tissue and/or a structure and/or a tissue boundary (e.g., a hollow organ). The hollow organ may include, for example, a vessel portion (e.g., an artery or a vein and/or a lung and/or a gut and/or a heart).

In one embodiment, the processing unit may be configured to determine and/or identify the region of interest on the representation area of the second display unit (e.g., in the second medical image data) based on the border of the hollow space. In the virtual mapping of the augmented reality onto the representation area of the second display unit, the border of the hollow space may be cut by a virtual plane that is, for example, parallel or tilted to the representation area of the second display unit. Therein, the cut border of the hollow space may have a, for example, closed or interrupted contour. The processing unit may be configured to determine and/or identify the contour of the cut border of the hollow space (e.g., in the virtual mapping of the augmented reality), for example, based on image values and/or contrast values. In one embodiment, the processing unit may be configured to determine and/or identify the region of interest as a, for example, coherent area that is bordered by the contour of the cut border. For example, the contour of the cut hollow space may delimit the spatial region of the transparency that is provided via the overlaying with the graphical representation of the augmented reality (e.g., the virtual window). In a two-dimensional design of the virtual window, the processing unit may be configured to determine the virtual window in a spatially limited manner, according to the region of interest (e.g., via the contour of the cut border of the hollow space). In a three-dimensional design of the virtual window, the processing unit may be configured to delimit the virtual window additionally along the depth dimension of the representation area via the border of the hollow space.

By this, a representation of the bordered hollow space that is close to reality, and its observation via the virtual window, may be enabled.

In a further embodiment of the representation apparatus, the processing unit may be configured to provide the graphical representation of the augmented reality having a virtual continuation of at least one object mapped in the second image data. Further, the first display unit may be configured to display the virtual continuation outside and/or adjoining the representation area of the second display unit.

In one embodiment, the processing unit may be configured to identify the at least one object (e.g., anatomical and/or medical and/or geometrical object) in the second medical image data, for example, based on image values and/or contrast values and/or a marker structure and/or an anatomy atlas. Therein, the identification of the at least one object in the second medical image data may include, for example, a segmentation. Further, the processing unit may be configured to identify an object in the first medical image data that corresponds to the at least one object, for example, based on the registration between the first medical image data and the second medical image data and/or based on image values and/or contrast values and/or a marker structure and/or an anatomy atlas. Therein, the identification of the at least one corresponding object in the second medical image data may include, for example, a segmentation. In one embodiment, the processing unit may further be configured to determine the virtual continuation having a mapping and/or a virtual representation (e.g., a model) of the corresponding object based on the first medical image data. Further, the processing unit may be configured to map the augmented reality virtually onto the representation area of the second display unit such that the virtual continuation in the operating state of the representation apparatus is displayed outside and/or adjoining the representation area of the second display unit. Therein, the virtual continuation may be arranged in a plane parallel to the representation area of the second display unit or having a predetermined angle in relation to the representation area.

By this, a display of the graphical representation of the augmented reality that is registered to the representation area of the second display unit and is not spatially delimited by the representation area may be enabled.

The present embodiments relate, in a second aspect, to a system including a representation apparatus (e.g., a plurality of representation apparatuses), a second display unit, and a medical imaging device. Therein, the medical imaging device is configured to record and/or provide the first medical image data and/or the second medical image data. Further, the second display unit is configured to display a graphical representation of the second medical image data on the representation area.

The advantages of the system substantially correspond to the advantages of the representation apparatus for displaying a graphical representation of an augmented reality. Features, advantages, or alternative embodiments mentioned herein may also be transferred to the other subject matter and vice versa.

In a further embodiment of the system, the medical imaging device may be configured to be arranged at least partially in an examination region of an examination object.

The medical imaging device may be configured, for example, as an endoscope (e.g., a laparoscope and/or a bronchoscope and/or a catheter). Therein, a distal portion of the medical imaging device may be arranged, in an operating state of the system, in the examination object (e.g., in a hollow organ of the examination object). In addition, the distal portion of the medical imaging device may be configured for recording the first medical image data and/or the second medical image data.

The present embodiments relate, in a third aspect, to a method for providing a graphical representation of an augmented reality. The relative positioning of a first display unit in relation to a representation area of a second display unit is captured by a capture unit. Further, graphical information is displayed on the representation area of the second display unit. Further, an observation geometry between the first display unit and the representation area of the second display unit is determined based on the relative positioning. In addition, a dataset is received. Further, the augmented reality is generated based on the dataset. Further, the graphical representation of the augmented reality is provided via a virtual mapping of the augmented reality onto the representation area of the second display unit along the observation geometry. Therein, the provision includes a display of the graphical representation of the augmented reality by the first display unit in at least partial overlaying with the graphical information on the representation area of the second display unit.

The advantages of the method substantially correspond to the advantages of the representation apparatus for displaying a graphical representation of an augmented reality. Features, advantages, or alternative embodiments mentioned herein may also be transferred to the other subject matter and vice versa. The apparatuses according to the present embodiments (e.g., the representation apparatus and/or the system) may be configured to carry out an embodiment of the method.

BRIEF DESCRIPTION OF THE DRAWINGS

Exemplary embodiments of the invention are illustrated in the drawings and are described in greater detail below. In the different figures, the same reference signs are used for the same features. In the figures.

DETAILED DESCRIPTION

Figure 1:
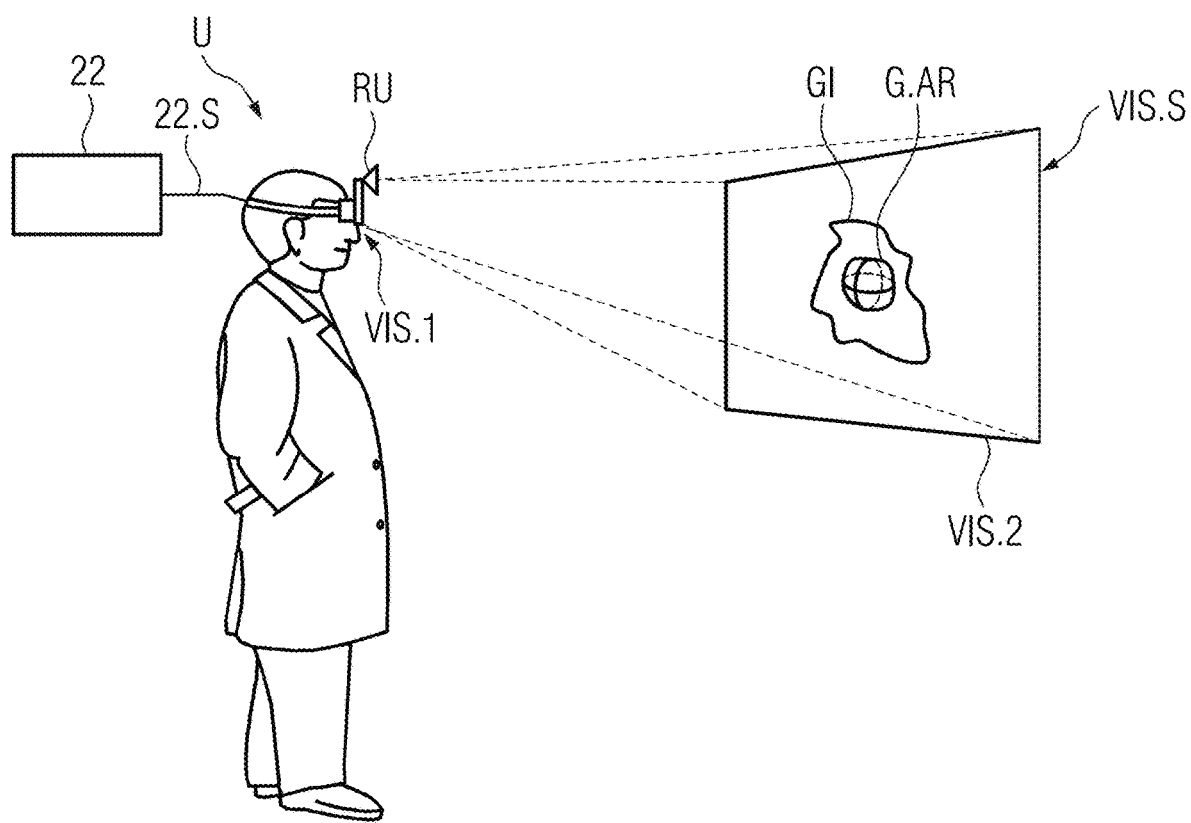
FIGS. 1 to 3 are schematic representations of different embodiments of a representation apparatus for displaying a graphical representation of an augmented reality.

FIG. 1 shows an embodiment of a representation apparatus for displaying a graphical representation of an augmented reality, illustrated schematically. The representation apparatus may have a capture unit RU, a first display unit VIS.1, and a processing unit 22. Therein, the first display unit VIS.1 may be configured to be at least partially transparent. Further, the capture unit RU may be configured to capture a relative positioning of the first display unit VIS.1 in relation to a representation area VIS.S of a second display unit VIS.2. The capture unit RU may have, for example, an optical and/or electromagnetic and/or acoustic sensor for capturing the relative positioning. Further, the representation area VIS.S of the second display unit VIS.2 may be configured to display graphical information GI. The second display unit VIS.2 may include, for example, a screen and/or a monitor and/or a projector and/or a projection area. Therein, the representation area VIS.S of the second display unit VIS.2 may include the projection area and/or a display layer of the screen and/or the monitor. For example, the representation area VIS.S of the second display unit VIS.2 may include a limited area on which the graphical information GI may be displayed. Therein, the representation area VIS.S of the second display unit VIS.2 may extend, at least partially (e.g., completely) flat (e.g., planar or curved). The graphical information GI may include image data (e.g., medical image data) and/or text information (e.g., operating parameters and/or object parameters of an object (medical object) and/or metadata regarding the medical image data.

In addition, the processing unit 22 is configured to determine an observation geometry between the first display unit VIS.1 and the representation area VIS.S of the second display unit VIS.2 based on the relative positioning. The processing unit 22 may be further configured to receive a dataset. In one embodiment, the processing unit 22 may be communicatively coupled to the first display unit VIS.1 and the capture unit RU, for example, by a signal 22.S. Further, the processing unit 22 may be configured to generate the augmented reality based on the dataset. Further, the processing unit 22 may be configured to provide a graphical representation G.AR of the augmented reality via a virtual mapping of the augmented reality onto the representation area VIS.S of the second display unit VIS.2 along the observation geometry.

The first display unit VIS.1 may be configured to display the graphical representation G.AR of the augmented reality in at least partial overlaying with the representation area VIS.S of the second display unit VIS.2 (e.g., stereoscopically). For this purpose, the first display unit VIS.1 may have, for example, a screen and/or a monitor and/or a projector and/or a projection area. In one embodiment, the first display unit VIS.1 may be configured as goggles (e.g., data goggles and/or a helmet, such as a data helmet). Further, the first display unit VIS.1 may be configured to be portable (e.g., wearable by a user U within a field of view of the user U).

Therein, the capture unit RU may be integrated at least partially into the first display unit VIS.1. In addition, the capture unit RU may have a defined (e.g., positionally fixed) arrangement in relation to the first display unit VIS.1. In one embodiment, the capture unit RU may be integrated at least partially into the first display unit VIS.1 such that the second display unit VIS.2 is arranged, in the operating state of the representation apparatus, in a capture region of the capture unit RU.

In one embodiment, the processing unit 22 may be further configured, given an altered relative positioning, to determine repeatedly the observation geometry between the first display unit VIS.1 and the representation area VIS.S of the second display unit VIS.2. In addition, the processing unit 22 may be configured, with a changed relative positioning, to provide the graphical representation G.AR of the augmented reality based on the most recently determined observation geometry.

The graphical representation G.AR of the augmented reality may have a graphical representation of at least one virtual object of the augmented reality. Therein, the capture unit RU may be configured to determine an observation parameter based on the relative positioning. Further, the processing unit 22 may be configured to determine the at least one virtual object based on the observation parameter. Alternatively or additionally, the processing unit 22 may be configured to adapt a resolution and/or scaling and/or size and/or positioning of the graphical representation of the at least one virtual object based on the observation parameter.

The capture unit RU may further be configured to capture an input and/or an identification of the user U who looks through the first display unit VIS.1 in an operating state of the representation apparatus. In addition, the capture unit RU may be configured to determine the observation parameter additionally based on the input and/or identification of the user U.

In one embodiment, the dataset may have a parameter relating to the graphical information GI that the second display unit VIS.2 displays in an operating state of the representation apparatus on the representation area VIS.S. Further, the processing unit 22 may be configured to generate the augmented reality dependent upon the parameter.

Figure 2:
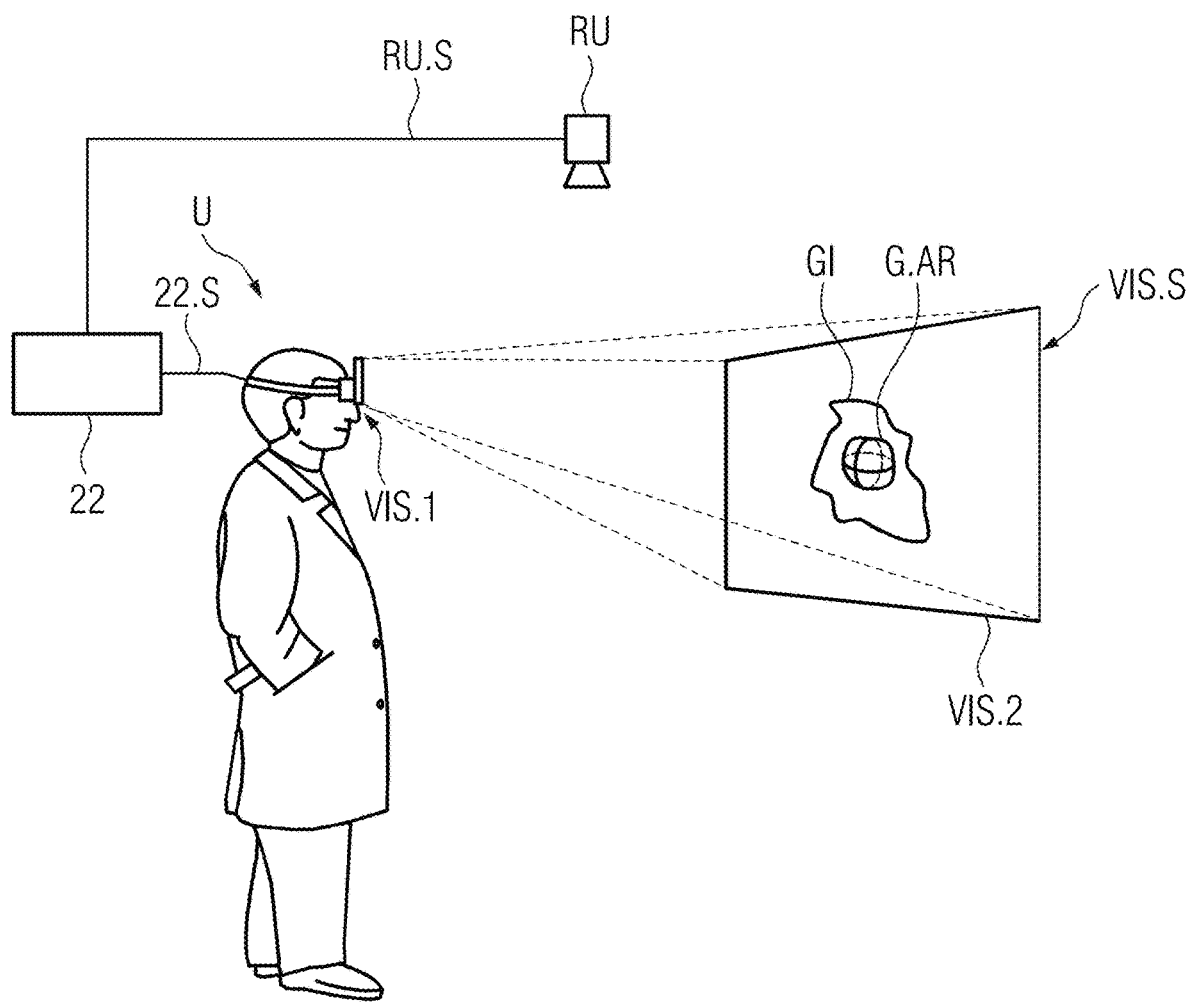

FIG. 2 shows a schematic representation of a further embodiment of the representation apparatus. Therein, the capture unit RU may be arranged, spaced from the first display unit VIS.1 and the second display unit VIS.2 (e.g., positionally fixed in relation to a room in which the first display unit VIS.1 and the second display unit VIS.2 are arranged in an operating state of the representation apparatus). In one embodiment, the capture unit RU may be arranged (e.g., positioned), such that the first display unit VIS.1 and the second display unit VIS.2 are arranged, in the operating state of the representation apparatus, in a capture region of the capture unit RU. In addition, the capture unit RU may be configured to directly capture the relative positioning based on physical features of the first display unit VIS.1 and the second display unit VIS.2.

Figure 3:
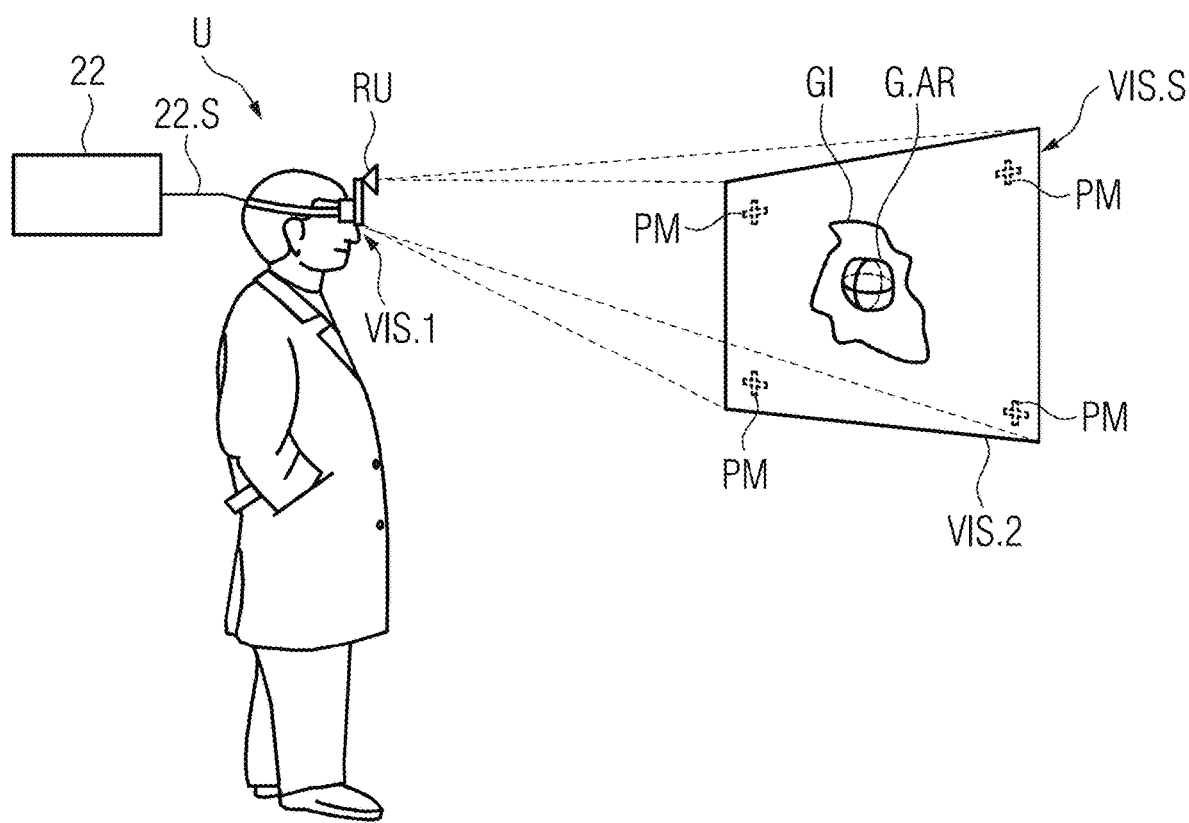

FIG. 3 shows schematically a further embodiment of the representation apparatus. Therein, the capture unit RU may be configured to capture the relative positioning based on a graphic marker structure PM displayed visibly and/or non-visibly on the representation area VIS.S of the second display unit VIS.2. The graphical marker structure PM may include a two-dimensional arrangement of graphical position markers of, for example, a geometrical form and/or a defined pattern that is stationary, for example, in relation to the representation area VIS.S of the second display unit VIS.2. Further, the capture unit RU may be configured to capture the relative positioning of the first display unit VIS.1 in relation to the representation area VIS.S of the second display unit VIS.2 based on the captured graphical marker structure (e.g., based on a spatial positioning of the graphical marker structure PM).

Figure 4:
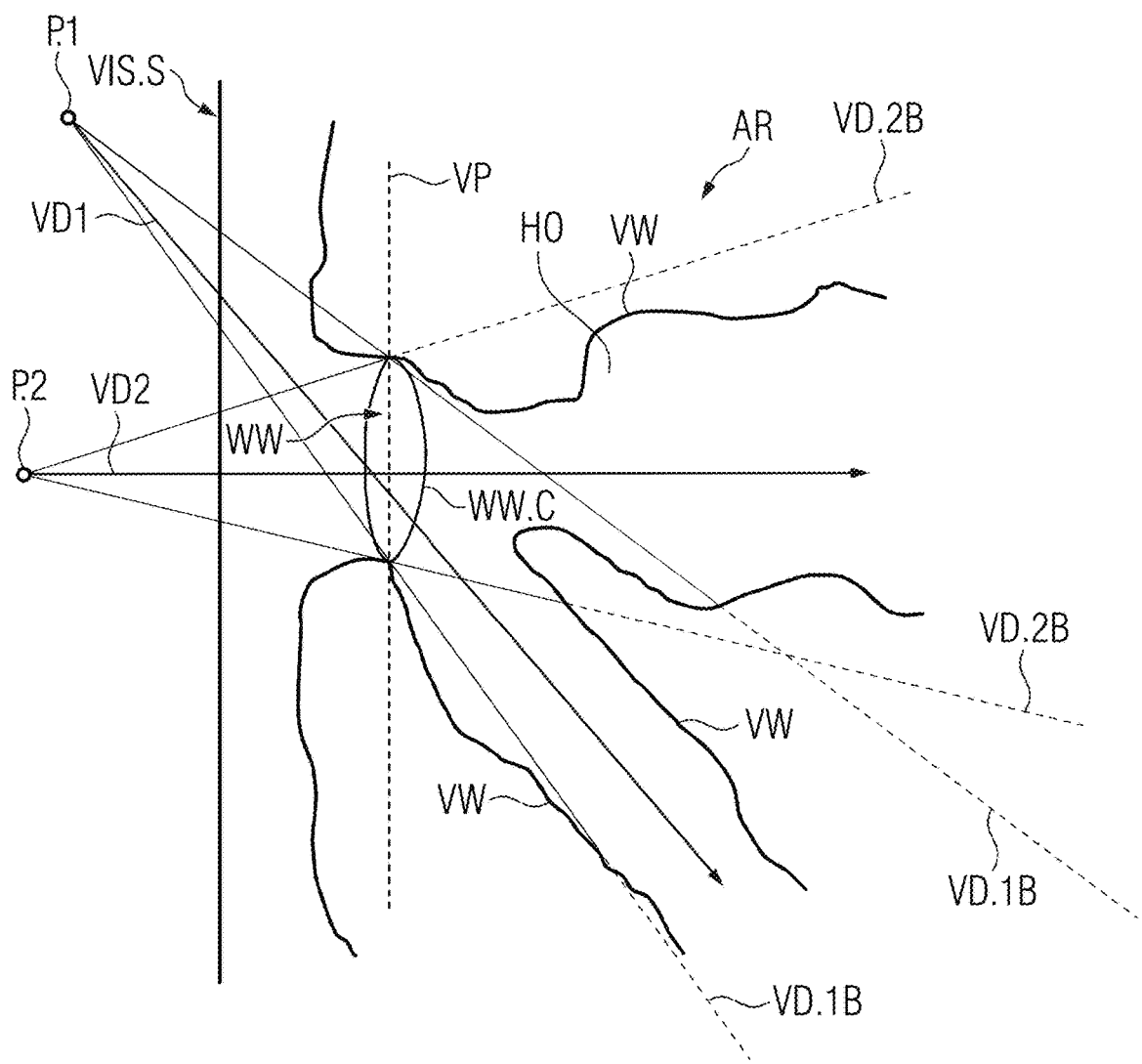
FIG. 4 is a schematic representation of an example of a virtual mapping of the augmented reality having a virtual window.

FIG. 4 shows a schematic representation of a virtual mapping of the augmented reality AR having a virtual window WW. Therein, the dataset may have first medical image data. In addition, the processing unit 22 may be further configured to generate the augmented reality AR based on the first medical image data. Further, in the operating state of the representation apparatus, the second display unit VIS.2 may display a graphical representation of second medical image data on the representation area VIS.S. Therein, the first medical image data and the second medical image data may form a mapping and/or a model of an at least partial shared examination region of an examination object.

In one embodiment, the first medical image data may map the examination object three-dimensionally. Further, the graphical representation G.AR of the augmented reality AR may be at least partially overlaid with the graphical representation of the second medical image data. Further, the processing unit 22 may be configured to provide the graphical representation G.AR of the augmented reality AR having a virtual window WW in relation to the graphical representation of the second image data.

In one embodiment, the shared region of the examination object may have a bordered hollow space HO (e.g., a hollow organ). The hollow organ may include, for example, a vessel portion (e.g., an artery or a vein and/or a lung and/or a gut structure and/or a heart). Therein, the virtual window WW may be delimited by the border VW of the hollow space HO cut from a virtual plane VP in the virtual mapping of the augmented reality AR onto the representation area VIS.S of the second display unit VIS.2. In the virtual mapping of the augmented reality AR onto the representation area VIS.S of the second display unit VIS.2, the border VW of the hollow space HO may be cut by the virtual plane VP, which is parallel, for example, to the representation area VIS.S of the second display unit VIS.2. Therein, the cut border VW of the hollow space HO may have a, for example, closed or interrupted contour WW.C. For example, the contour WW.C of the cut border VW of the hollow space HO may delimit the spatial region of the transparency that is provided by the overlaying, with the graphical representation G.AR, of the augmented reality AR (e.g., the virtual window WW). In one embodiment, the processing unit 22 may be configured to determine the virtual window WW in a spatially limited manner, according to the border VW of the hollow space HO cut by the virtual plane VP (e.g., according to the contour WW.C). In a three-dimensional design of the virtual window WW, the processing unit 22 may be configured to delimit the virtual window WW additionally along the depth dimension of the representation area VIS.S via the border VW of the hollow space HO. For illustration, in FIG. 4, two exemplary observation positions P.1 and P.2 of the user U looking through the first display unit are shown. Therein, the display of the graphical representation of the second image data overlaid with the graphical representation G.AR of the augmented reality AR may be observed by the user U on the representation area VIS.S of the second display unit VIS.2 dependent upon the observation position P.1 or P.2 (e.g., momentary observation position P.1 or P.2) with a different viewing direction VD.1 or VD.2. Therein, the limit rays VD.1B to the viewing direction VD.1 and the limit rays VD2.B to the viewing direction VD.2 illustrate the limitation (e.g., visual limitation) of the virtual window WW along the depth dimension of the representation area VIS.S by the border VW of the hollow space HO. Therein, the virtual mapping of the augmented reality AR onto the representation area VIS.S of the second display unit VIS.2 for providing the graphical representation G.AR of the augmented reality AR may be based, for example, on a virtual projection mapping and/or ray-tracing and/or a rendering in accordance with a mapping matrix (e.g., a mapping matrix and/or camera matrix of the medical imaging device for recording and/or for providing the first medical image data), along the observation geometry (e.g., dependent upon the observation position P.1 or P.2 and/or the viewing direction VD.1 or VD.2 of the user U).

Figure 5:
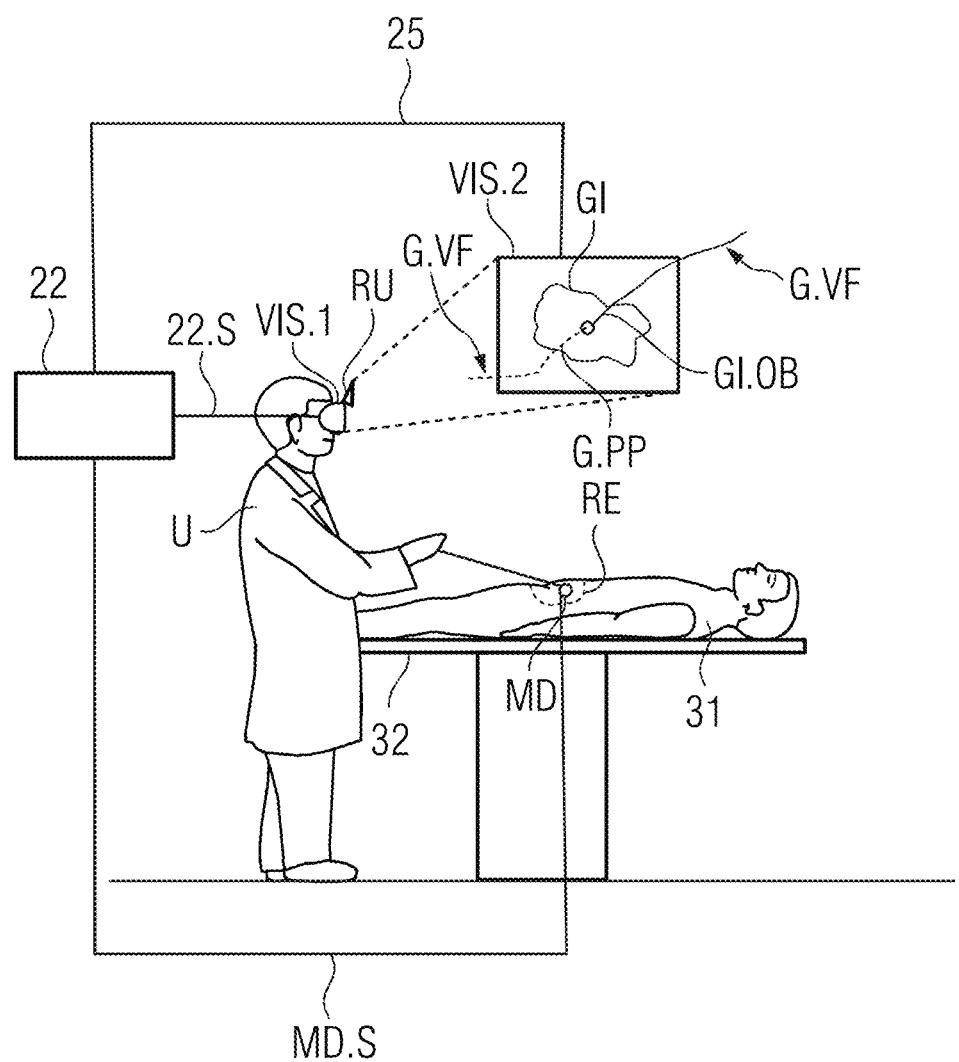
FIG. 5 is a schematic representation of an embodiment of a system.

FIG. 5 shows schematically one embodiment of a system. The system may have the representation apparatus, the second display unit VIS.2, and a medical imaging device MD. Therein, the medical imaging device MD may be configured to be arranged at least partially in an examination region RE (e.g., a hollow organ of an examination object 31 arranged on a patient positioning apparatus 32). In one embodiment, the medical imaging device MD may be configured to record and/or provide the first medical image data and/or the second medical image data. Further, the second display unit VIS.2 may be configured to display the graphical representation of the second medical image data on the representation area VIS.S.

The processing unit 22 may be configured to provide the graphical representation G.AR of the augmented reality AR having a virtual continuation G.VG of at least one object mapped in the second image data (e.g., an anatomical and/or medical and/or geometric object G.OB). FIG. 5 shows, by way of example, a hollow organ as the at least one object GI.OB mapped in the second image data. Therein, the first display unit VIS.1 may be configured to display the virtual continuation G.VF outside and/or adjoining the representation area VIS.S of the second display unit VIS.2. Therein, the virtual continuation G.VF may have an item of graphical path planning information G.PP for a medical object and/or for the medical imaging device MD in the hollow organ.

Figure 6:
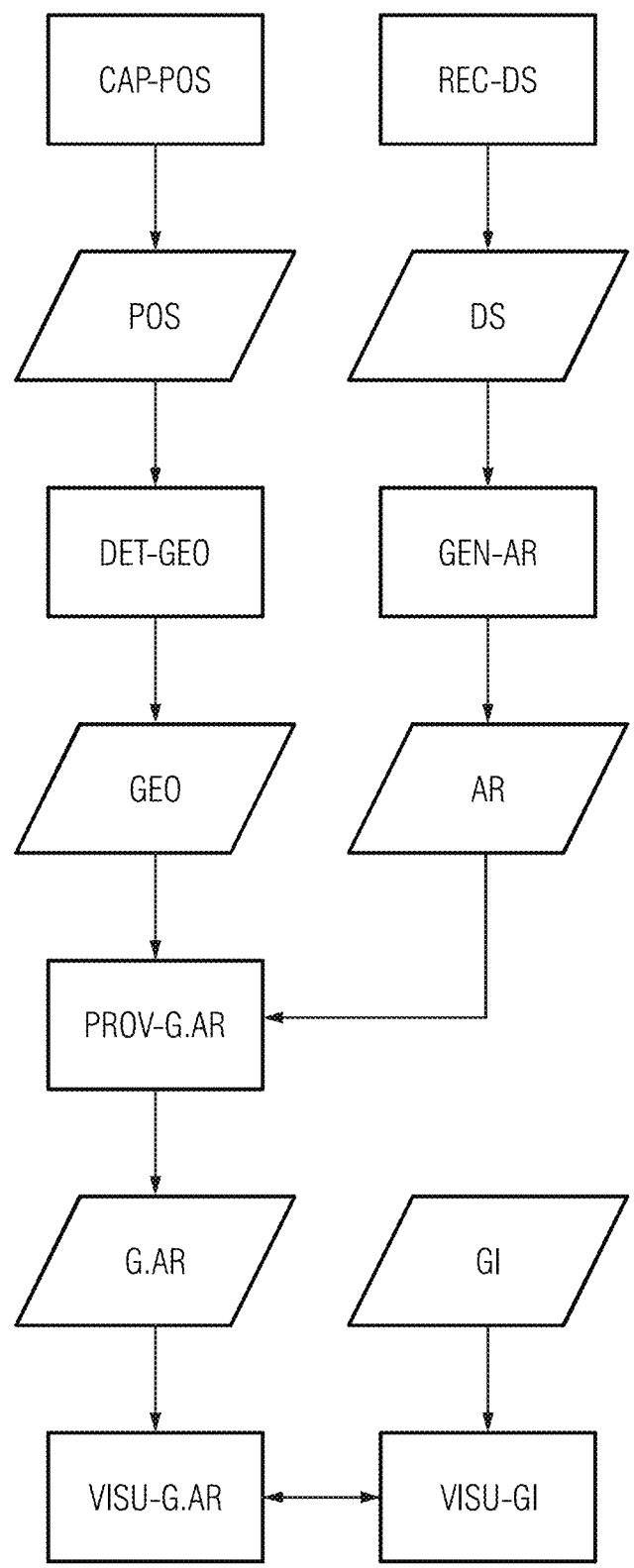
FIG. 6 is a schematic representation of one embodiment of a method for providing a graphical representation of an augmented reality.

FIG. 6 shows schematically an embodiment of a method for providing PROV-G.AR a graphical representation G.AR of an augmented reality AR. Therein, the relative positioning POS of the first display unit VIS.1 in relation to the representation area VIS.S of the second display unit VIS.2 may be captured by the capture unit RU. Further, the graphical information GI may be displayed VISU-GI on the representation area VIS.S of the second display unit VIS.2. Further, the observation geometry GEO between the first display unit VIS.1 and the representation area VIS.S of the second display unit VIS.2 may be determined DET-GEO based on the relative positioning POS. In addition, the dataset DS may be received REC-DS. Further, the augmented reality AR may be generated GEN-AR based on the dataset DS. Further, the graphical representation of the augmented reality G.AR may be provided PROV-G.AR via the virtual mapping of the augmented reality AR onto the representation area VIS.S of the second display unit VIS.2 along the observation geometry GEO. Therein, the provision PROV-G.AR may include a display VISU-G.AR of the graphical representation of the augmented reality G.AR using the first display unit VIS.1 in at least partial overlaying with the graphical information GI on the representation area VIS.S of the second display unit VIS.2.

The schematic representations contained in the drawings described do not show any scale or size relationship.

The methods and apparatuses described above in detail merely involve exemplary embodiments that may be modified by a person skilled in the art in a wide variety of ways without departing from the scope of the invention. Further, the use of the indefinite article "a" or "an" does not preclude the possibility that the relevant features may also be present plurally. Similarly, the expressions "unit" and "element" do not preclude the components in question consisting of a plurality of cooperating subcomponents that may possibly also be spatially distributed.

The advantage of the present embodiments is the method and device enable effective detection of tumor region in the medical image. Further, the present embodiments enable identification of right feeder vessels for embolization. Therefore, healthy tissues associated with the patient are not damaged due to cancer therapy. Additionally, the present embodiments reduce the need for manual identification of tumor region in the medical images. The present embodiments further enable targeted cancer therapy based on which the tumor blood vessel network may be embolized accurately. Further, the present embodiments enable multiple tumors to be embolized in one medical procedure.

The foregoing examples have been provided merely for the purpose of explanation and are in no way to be construed as limiting of the present e disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods, and uses, such as are within the scope of the appended claims. Those skilled in the art, having the benefit of the teachings of this specification, may effect numerous modifications thereto, and changes may be made without departing from the scope and spirit of the invention in its aspects.

The invention claimed is:

1. A representation apparatus for displaying a graphical representation of an augmented reality, the representation apparatus comprising:
   a capture unit;
   a first display unit; and
   a processing unit,
   wherein the first display unit is configured to be at least partially transparent,
   wherein the capture unit is configured to capture a relative positioning of the first display unit in relation to a representation area of a second display unit,
   wherein the representation area of the second display unit is configured to display graphical information,
   wherein the processing unit is configured to:
      determine an observation geometry between the first display unit and the representation area of the second display unit based on the relative positioning;
      receive a dataset;
      generate the augmented reality based on the dataset; and
      provide the graphical representation of the augmented reality via a virtual mapping of the augmented reality onto the representation area of the second display unit along the observation geometry, and
   wherein the first display unit is configured to display the graphical representation of the augmented reality in at least partial overlaying with the representation area of the second display unit.

2. The representation apparatus of claim 1, wherein the processing unit is further configured, in the event of a changed relative positioning, to:
   determine the observation geometry between the first display unit and the representation area of the second display unit repeatedly; and
   provide the graphical representation of the augmented reality based on a most recently determined observation geometry.

3. The representation apparatus of claim 1, wherein the capture unit is arranged spaced from the first display unit and the second display unit or is integrated at least partially into the first display unit or the second display unit.

4. The representation apparatus of claim 1, wherein the capture unit has an optical sensor, an electromagnetic sensor, an acoustic sensor, or any combination thereof for capturing the relative positioning.

5. The representation apparatus of claim 1, wherein the capture unit is configured to capture the relative positioning based on physical features of the first display unit, the second display unit, or the first display unit and the second display unit, based on a graphic marker structure displayed visibly, non-visibly, or visibly and non-visibly on the representation area of the second display unit, or a combination thereof.

6. The representation apparatus of claim 1, wherein the graphical representation of the augmented reality has a graphical representation of at least one virtual object of the augmented reality,
wherein the capture unit is configured to determine an observation parameter based on the relative positioning,
wherein the processing unit is configured to:
determine the at least one virtual object based on the observation parameter;
adapt a resolution, scaling, a size, positioning, or any combination thereof of the graphical representation of the at least one virtual object based on the observation parameter; or
a combination thereof.

7. The representation apparatus of claim 6, wherein the capture unit is further configured to:
capture an input, an identification, or the input and the identification of a user who looks through the first display unit in an operating state of the representation apparatus; and
determine the observation parameter also based on the input, the identification, or the input and the identification of the user.

8. The representation apparatus of claim 1, wherein the dataset has a parameter relating to the graphical information, which the second display unit displays on the representation area in an operating state of the representation apparatus, and
wherein the processing unit is further configured to generate the augmented reality dependent upon the parameter.

9. The representation apparatus of claim 1, wherein the dataset includes first medical image data,
wherein the processing unit is configured to generate the augmented reality based on the first medical image data,
wherein in the operating state of the representation apparatus:
the second display unit is configured to display a graphical representation of second medical image data as the graphical information on the representation area, wherein, the first medical image data and the second medical image data have a mapping, a model, or the mapping and the model of an at least partially common examination region of an examination object; and
the graphical representation of the augmented reality is at least partially overlaid with the graphical representation of the second medical image data.

10. The representation apparatus of claim 9, wherein the first image data maps, models, or maps and models the examination object three-dimensionally, and
wherein the processing unit is configured to provide the graphical representation of the augmented reality having a virtual window in relation to the graphical representation of the second image data.

11. The representation apparatus of claim 10, wherein the common examination region of the examination object has a bordered hollow space, and
wherein the virtual window is delimited by the border of the hollow space cut from a virtual plane in the virtual mapping of the augmented reality onto the representation area of the second display unit.

12. The representation apparatus of claim 9, wherein the processing unit is configured to provide the graphical representation of the augmented reality having a virtual continuation of at least one object mapped into the second image data, and
wherein the first display unit is configured to display the virtual continuation outside, adjoining, or outside and adjoining the representation area of the second display unit.

13. A system comprising:
a representation apparatus for displaying a graphical representation of an augmented reality, the representation apparatus comprising:
a capture unit;
a first display unit; and
a processing unit, wherein the first display unit is configured to be at least partially transparent, wherein the capture unit is configured to capture a relative positioning of the first display unit in relation to a representation area of a second display unit, wherein the representation area of the second display unit is configured to display graphical information, wherein the processing unit is configured to determine an observation geometry between the first display unit and the representation area of the second display unit based on the relative positioning, receive a dataset, generate the augmented reality based on the dataset, and provide the graphical representation of the augmented reality via a virtual mapping of the augmented reality onto the representation area of the second display unit along the observation geometry, wherein the first display unit is configured to display the graphical representation of the augmented reality in at least partial overlaying with the representation area of the second display unit, wherein the dataset includes first medical image data, wherein the processing unit is configured to generate the augmented reality based on the first medical image data, and wherein in the operating state of the representation apparatus, the second display unit is configured to display a graphical representation of second medical image data as the graphical information on the representation area, the first medical image data and the second medical image data having a mapping, a model, or the mapping and the model of an at least partially common examination region of an examination object, and the graphical representation of the augmented reality is at least partially overlaid with the graphical representation of the second medical image data;
the second display unit; and
a medical imaging device,
wherein the medical imaging device is configured to record, provide, or record and provide the first medical image data, the second medical image data, or the first medical image data and the second medical image data, and
wherein the second display unit is configured to display a graphical representation of the second medical image data on the representation area.

14. The system of claim 13, wherein the medical imaging device is arrangeable at least partially in an examination region of an examination object.

15. A method for providing a graphical representation of an augmented reality, the method comprising:
- capturing, by a capture unit, a relative positioning of a first display unit in relation to a representation area of a second display unit;
- displaying graphical information on the representation area of the second display unit;
- determining an observation geometry between the first display unit and the representation area of the second display unit based on the relative positioning;
- receiving a dataset;
- generating the augmented reality based on the dataset; and
- providing the graphical representation of the augmented reality via a virtual mapping of the augmented reality onto the representation area of the second display unit along the observation geometry, the providing comprising displaying the graphical representation of the augmented reality by the first display unit in at least partial overlaying with the graphical information on the representation area of the second display unit.

16. The method of claim 15, wherein in the event of a changed relative positioning, the method further comprises:
- determining the observation geometry between the first display unit and the representation area of the second display unit repeatedly; and
- providing the graphical representation of the augmented reality based on a most recently determined observation geometry.

17. The method of claim 15, wherein capturing the relative positioning comprises capturing, by the capture unit, the relative positioning based on physical features of the first display unit, the second display unit, or the first display unit and the second display unit, based on a graphic marker structure displayed visibly, non-visibly, or visibly and non-visibly on the representation area of the second display unit, or a combination thereof.

18. The method of claim 15, wherein the graphical representation of the augmented reality has a graphical representation of at least one virtual object of the augmented reality,
wherein the method further comprises:
- determining, by the capture unit, an observation parameter based on the relative positioning; and
- determining the at least one virtual object based on the observation parameter, adapting a resolution, scaling, a size, positioning, or any combination thereof of the graphical representation of the at least one virtual object based on the observation parameter, or a combination thereof.

\* \* \* \* \*